United States Patent [19]

Jan et al.

[11] Patent Number: 5,354,931
[45] Date of Patent: Oct. 11, 1994

[54] PROCESS FOR HYDROTREATING AN ORGANIC FEEDSTOCK CONTAINING OXYGEN COMPOUNDS AND A HALOGEN COMPONENT

[75] Inventors: Chwu-Ching Jan; Mark D. Moser, both of Elk Grove Village; Tom N. Kalnes, La Grange; George R. Hibel, Schaumburg, all of Ill.

[73] Assignee: UOP, Des Plaines, Ill.

[21] Appl. No.: 28,862

[22] Filed: Mar. 10, 1993

[51] Int. Cl.$^5$ .................. C07C 5/00; C01B 7/01; C01B 7/07; C10G 25/00
[52] U.S. Cl. .................. 585/264; 585/733; 585/802; 423/481; 423/488; 208/91; 208/179; 208/262.5
[58] Field of Search .......... 585/733, 264, 802; 423/481, 488; 208/179, 91, 262.5

[56] References Cited

U.S. PATENT DOCUMENTS

| | | | |
|---|---|---|---|
| 4,059,677 | 11/1977 | Sare et al. | 423/488 |
| 4,818,368 | 4/1989 | Kalnes et al. | 208/50 |
| 4,839,153 | 6/1989 | Schmidhammer et al. | 423/488 |
| 4,882,037 | 11/1989 | Kalnes et al. | 208/85 |
| 4,923,590 | 5/1990 | Kalnes et al. | 208/85 |

Primary Examiner—Helen M. S. Sneed
Assistant Examiner—E. D. Irzinski
Attorney, Agent, or Firm—Thomas K. McBride; John G. Tolomei; John G. Cutts, Jr.

[57] ABSTRACT

The invention provides a process for hydrotreating an organic feedstock containing oxygen compounds and a halogen component by means of removing the oxygen compounds with an adsorbent and then contacting the resulting organic feedstock having a reduced concentration of oxygen compounds and a gaseous recycle stream containing hydrogen with a hydrogenation catalyst in a hydrogenation reaction zone to produce an anhydrous liquid stream comprising hydrogenated hydrocarbonaceous compounds having a reduced concentration of halogen and a hydrogen halide compound. The resulting effluent from the hydrogenation zone is optionally separated to produce a hydrogenated hydrocarbonaceous stream having a reduced level of halogen and an anhydrous stream comprising a hydrogen halide compound.

14 Claims, 1 Drawing Sheet

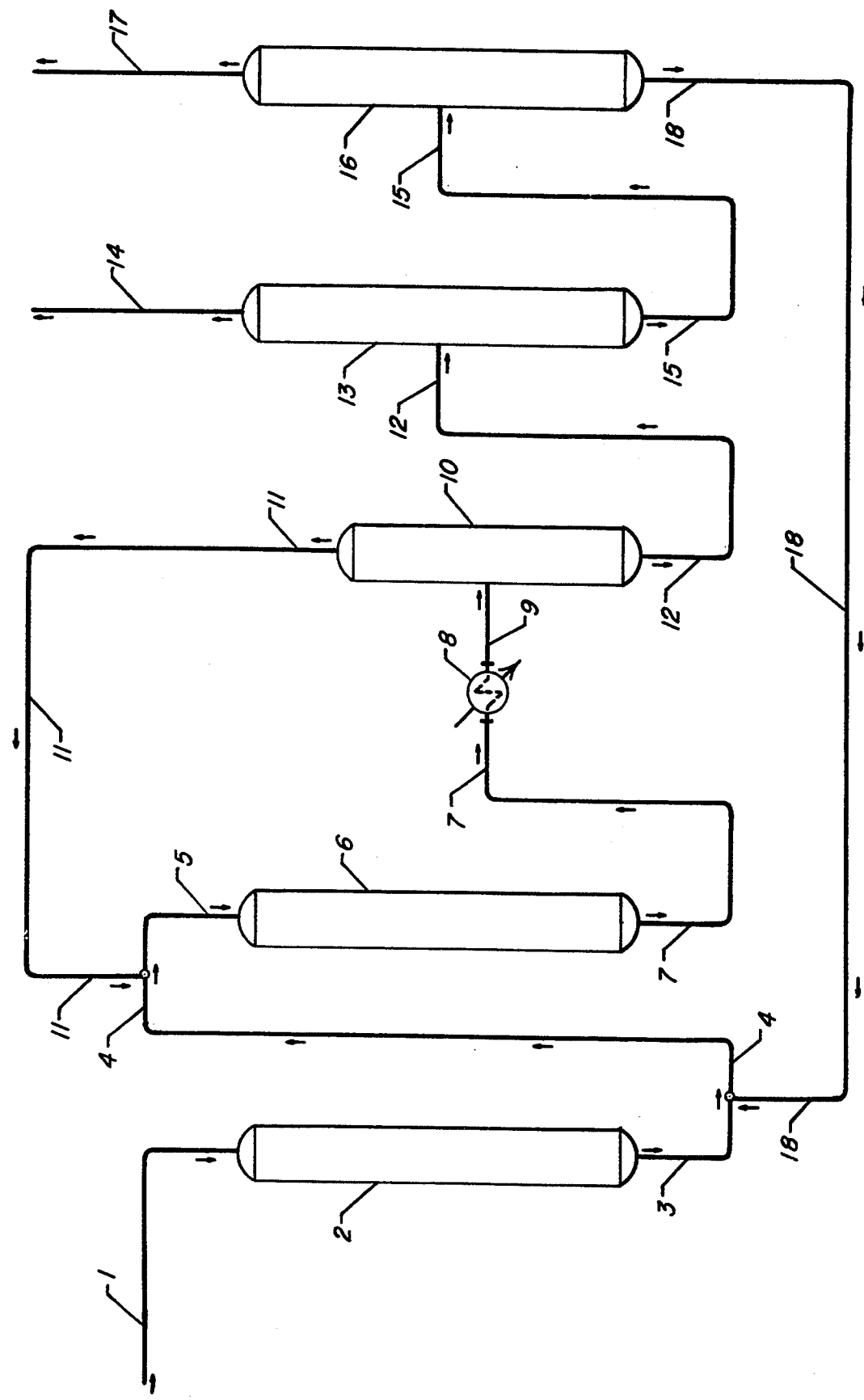

PROCESS FOR HYDROTREATING AN ORGANIC FEEDSTOCK CONTAINING OXYGEN COMPOUNDS AND A HALOGEN COMPONENT

BACKGROUND OF THE INVENTION

The field of art to which this invention pertains is the conversion of an organic feedstock which contains oxygen compounds and a halogen component to produce hydrocarbonaceous compounds having a reduced concentration of halogen moieties.

There has always been a demand for the conversion or disposal of waste or by-product streams which originate in the petroleum chemical and petrochemical industries. More particularly, these by-products originate from the chlorination of olefins in the production of epichlorohydrin, propylene oxide and vinyl chloride monomers, for example. It is common in such streams for the predominate species to be halogenated alkanes, but, in addition, in some cases, there are present oxygen compounds such as aldehydes and ketones that can subsequently decompose to water during subsequent processing, thereby leading to the undesirable corrosion of the reactor and its associated piping. This production of water leads to formation of corrosive aqueous solutions and the contamination of any desired anhydrous hydrogen halide product streams. Previous techniques utilized to dispose of waste streams containing halogen components, oxygen compounds and other heteroatomic compounds have frequently become environmentally unpopular or illegal and, in general, have always been expensive. With the increased environmental emphasis for the treatment and recycle of halogenated organic compounds, there is an increased need for the conversion of these products when they become unwanted. Therefore, those skilled in the art have sought to find feasible techniques to convert such feedstocks to provide hydrocarbonaceous product streams having a reduced concentration of halogen which may be safely and usefully employed or recycled. Previous techniques which have been employed include incineration and dumping which, in addition to potential pollution considerations, fail to recover valuable hydrocarbonaceous materials and the resulting halogen compounds.

Recently the prior art has disclosed various processes for the conversion of halogenated organic streams to dispose of the streams, to produce hydrocarbons and halides, to recycle valuable raw materials, or a combination thereof. However, at least some of the halogenated organic streams which are candidates for conversion have been discovered to contain small quantities of oxygen compounds. We have discovered an improved process which is capable of successfully processing an organic feedstock containing oxygen compounds and a halogen component.

INFORMATION DISCLOSURE

In U.S. Pat. No. 4,818,368 (Kalnes et al), a process is disclosed for treating a temperature-sensitive hydrocarbonaceous stream containing a non-distillable component to produce a hydrogenated distillable hydrocarbonaceous product while minimizing the degradation of the hydrocarbonaceous stream.

In U.S. Pat. No. 4,882,037 (Kalnes et al), a process is disclosed for treating a temperature-sensitive hydrocarbonaceous stream containing a non-distillable component and a distillable, hydrogenatable hydrocarbonaceous fraction to produce a selected hydrogenated distillable light hydrocarbonaceous product, a distillable heavy hydrocarbonaceous liquid product and a heavy product.

In U.S. Pat. No. 4,923,590 (Kalnes et al), a process is disclosed wherein the effluent from a hydrogenation reaction zone is contacted with an aqueous scrubbing solution. In one embodiment, the '590 patent teaches that when the feed to the hydrogenation zone comprises halogenated compounds, the aqueous scrubbing solution preferably contains a basic compound to neutralize the acid.

BRIEF SUMMARY OF THE INVENTION

The present invention provides a process for hydrotreating an organic feedstock containing oxygen compounds and a halogen component by means of removing the oxygen compounds in an adsorption zone and subsequently contacting the resulting organic feed having a reduced level of oxygen compounds and a gaseous recycle stream containing hydrogen with a hydrogenation catalyst in a hydrogenation reaction zone to produce an anhydrous liquid stream comprising hydrogenated hydrocarbonaceous compounds having a reduced concentration of halogen and a hydrogen halide compound. The resulting effluent from the hydrogenation zone is separated to produce a hydrogen-rich gaseous recycle stream. Important elements of the improved process are the essentially complete elimination of water in the effluent from the hydrogenation zone, the ability to achieve longer run lengths and catalyst life, and the use of more economical metallurgy in the processing plant. In addition to these operating advantages, valuable products including hydrogenated hydrocarbonaceous compounds and hydrogen halide compounds are produced while simultaneously converting unwanted by-products or wastes to thereby solve a potential pollution problem.

One embodiment of the invention may be characterized as a process for treating a halogenated organic stream containing oxygen compounds to produce an anhydrous liquid stream comprising hydrogenated hydrocarbonaceous compounds and a hydrogen halide compound which process comprises the steps of: (a) contacting the halogenated organic stream containing oxygen compounds with a selective adsorbent at adsorption-promoting conditions in an adsorption zone to selectively remove at least a portion of the oxygen compounds; (b) contacting a resulting halogenated organic stream having a reduced concentration of oxygen compounds produced in step (a) and a hydrogen-rich, gaseous recycle stream with a hydrogenation catalyst in a hydrogenation reaction zone at hydrogenation reaction conditions to increase the hydrogen content of the halogenated organic stream and to thereby produce a hydrogen halide compound; and (c) condensing at least a portion of the resulting effluent from the hydrogenation reaction zone to produce the hydrogen-rich, gaseous recycle stream and an anhydrous liquid stream comprising hydrogenated hydrocarbonaceous compounds and a hydrogen halide compound.

Another embodiment of the invention my be characterized as a process for treating a halogenated organic stream containing oxygen compounds to produce a hydrogenated hydrocarbonaceous stream having a reduced level of halogen and an anhydrous stream comprising a hydrogen halide compound which process comprises the steps of: (a) contacting the halogenated organic stream containing oxygen compounds with a selective adsorbent at adsorption-promoting conditions in an adsorption zone to selectively remove at least a portion of the oxygen compounds; (b) contacting a resulting halogenated organic stream having a reduced concentration of oxygen compounds produced in step (a) and a hydrogen-rich, gaseous recycle stream with a hydrogenation catalyst in a hydrogenation reaction zone at hydrogenation reaction conditions to increase the hydrogen content of the halogenated organic stream and to thereby produce a hydrogen halide compound; (c) condensing at least a portion of the resulting effluent from the hydrogenation reaction zone to produce the hydrogen-rich, gaseous recycle stream and a liquid stream comprising hydrogenated hydrocarbonaceous compounds and a hydrogen halide compound; and (d) separating the liquid stream comprising hydrogenated hydrocarbonaceous compounds and a hydrogen halide compound to produce an anhydrous stream comprising a hydrogen halide compound and a stream comprising hydrogenated hydrocarbonaceous compounds.

Yet another embodiment of the invention may be characterized as a process for treating a halogenated organic stream containing oxygen compounds to produce a hydrogenated hydrocarbonaceous stream having a reduced level of halogen and an anhydrous stream comprising a hydrogen halide compound which process comprises the steps of: (a) contacting the halogenated organic stream containing oxygen compounds with a selective adsorbent at adsorption-promoting conditions in an adsorption zone to selectively remove at least a portion of the oxygen compounds; (b) contacting a resulting halogenated organic stream having a reduced concentration of oxygen compounds produced in step (a), a hydrogen-rich, gaseous recycle stream and a recycle stream comprising unreacted halogenated organic compounds with a hydrogenation catalyst in a hydrogenation reaction zone at hydrogenation reaction conditions to increase the hydrogen content of the halogenated organic stream and to thereby produce a hydrogen halide compound; (c) condensing at least a portion of the resulting effluent from the hydrogenation reaction zone to produce the hydrogen-rich, gaseous recycle stream and a liquid stream comprising hydrogenated hydrocarbonaceous compounds and a hydrogen halide compound; (d) separating the liquid stream comprising hydrogenated hydrocarbonaceous compounds and a hydrogen halide compound to produce an anhydrous stream comprising a hydrogen halide compound and a stream comprising hydrogenated hydrocarbonaceous compounds and unreacted halogenated organic compounds; and (e) separating the stream comprising hydrogenated hydrocarbonaceous compounds and unreacted halogenated organic compounds to produce the recycle stream comprising unreacted halogenated organic compounds and the hydrogenated hydrocarbonaceous stream having a reduced level of halogen.

Other embodiments of the present invention encompass further details such as preferred feedstocks, hydrogenation catalysts and operating conditions, all of which are hereinafter disclosed in the following discussion of each of these facets of the invention.

BRIEF DESCRIPTION OF THE DRAWING

The drawing is a simplified process flow diagram of a preferred embodiment of the present invention.

DETAILED DESCRIPTION OF THE INVENTION

The present invention provides an improved integrated process for hydrotreating an organic feedstock containing oxygen compounds and a halogen component while eliminating or at least minimizing the production of water during processing and thereby minimizing the production of corrosive aqueous solutions in the process plant and permitting the production of anhydrous hydrogen halide product. There is a steadily increasing demand for technology which is capable of converting or hydrotreating an organic feedstock containing a halogen component and, in particular, for a process which is capable of processing such a stream which, in addition, contains oxygen compounds. In accordance with the present invention, it has been unexpectedly discovered that the oxygen compounds may be selectively removed from an organic feedstock containing halogen compounds and oxygen compounds without the undesirable conversion of the halogen compounds during the removal of the oxygen compounds.

A wide variety of halogenated organic compounds containing oxygen compounds are candidates for feed streams in accordance with the process of the present invention. Examples of organic streams comprising halogenated organic compounds which are suitable for treatment by the process of the present invention are dielectric fluids, hydraulic fluids, heat transfer fluids, used lubricating oil, used cutting oils, used solvents, halogenated hydrocarbonaceous by-products, oils contaminated with polychlorinated biphenyls (PCB), halogenated wastes, by-products from the manufacture of vinyl chloride monomer, propylene oxide, allyl chloride, epichlorohydrin and other halogenated intermediates and final products, petrochemical by-products and other halogenated hydrocarbonaceous industrial wastes. Often, in a particular place or location, two or more halogenated organic streams are present and require further treatment. The halogenated organic compounds may also contain hydrogen and are therefore then referred to as hydrocarbonaceous compounds. The halogenated organic feed to the present process preferably contains oxygen compounds in an amount from about 50 to about 1000 weight ppm. The halogenated organic feed also preferably contains halogenated organic compounds in an mount from about 50 to about 99 weight percent.

Preferred feedstocks comprise a component selected from the group consisting of fractionation column bottoms from the production of allyl chloride, fractionation column bottoms from the production of ethylene dichloride, by-products from the manufacture of vinyl chloride monomer, fractionation column bottoms from the production of trichloroethylene and perchloroethylene, used dielectric fluid containing polychlorinated biphenyls (PCB) and halogenated benzene, used solvents, fractionation bottoms from the purification column in epichlorohydrin production, carbon tetrachloride, 1,1,1-trichloroethane, halogenated alcohols, halogenated ethers, chlorofluorocarbons and admixtures thereof.

The process of the present invention is most advantageously utilized when the feedstock contains oxygen compounds which have a marked tendency to be convened to water when subjected to a hydrogenation zone in the presence of hydrogen. In accordance with the present invention, the halogenated organic feedstock preferably contains from about 50 to about 1000 weight ppm of oxygen compounds or water precursors. It is preferred that the oxygen compounds are selected from the group consisting of water, aldehydes, ketones, alcohols and ethers. In one embodiment of the present invention, the resulting hydrogen halide may be conveniently recovered as an anhydrous hydrogen halide stream and, as used herein, the term "anhydrous stream comprising hydrogen halide" connotes a stream having less than about 50 ppm by weight of water.

The halogenated organic compounds which are contemplated as feedstocks in the present invention may contain a halogen selected from the group consisting of chlorine, bromine, fluorine and iodine. Preferred halogen compounds contain a halogen selected from the group consisting of chlorine and fluorine. In addition, the halogenated organic compounds preferably contain from 1 to about 20 carbon atoms per molecule.

In accordance with the present invention, a halogenated organic feedstock containing oxygen compounds is contacted with a selective adsorbent at adsorption-promoting conditions in an adsorption zone to selectively remove at least a portion of the oxygen compounds. The adsorbent, which may function as a physical or as a chemical adsorbent, is preferably disposed as a fixed bed in two or more cylindrical contacting chambers. The flow of the feedstock containing oxygen compounds is preferably switched between different chambers to allow continuous processing while the adsorbent in the chambers which are not being used is either regenerated or replaced, depending on the regenerability and remaining capacity of the adsorbent. The adsorbent may also be contained in a different chamber configuration such as a moving bed or a fluidized bed, for example.

The required adsorption-promoting conditions will depend on such factors as the specific adsorbent used in the process and the oxygen compounds to be removed from the feedstock. A general range of suitable adsorption-promoting conditions includes a superatmospheric pressure less than about 500 psig, although higher pressures my be employed, and a temperature less than about 200° F. (93° C.). A liquid hourly space velocity of less than about 60 hr$^{-1}$ is preferred. A preferred range of adsorption-promoting conditions includes a pressure from about 5 to about 300 psig, a temperature from about 50° F. (10° C.) to about 200° F. (93° C.) and a liquid hourly space velocity from about 0.1 to about 50 hr$^{-1}$.

The adsorbent is preferably in the form of solid spherical particles on the order of about 1/16 to about 1/4 of an inch in diameter. The preferred adsorbents are the zeolitic materials known as molecular sieves and ion exchange resins. The selection of adsorbents for use in the present process is dependent on the effectiveness, selectivity and regenerability of the particular adsorbent and is not dependent on the manner in which the adsorbent acts to remove the oxygen compounds. The adsorbent may therefore act by physical or chemical adsorption or by ion exchange. As is known to those skilled in the art, these materials are normally selective as to the compounds they tend to adsorb, and it is therefore necessary to carefully select the proper materials. Small scale testing may be required in some instances as part of the selection process to determine the appropriateness of materials other than those listed herein. It is contemplated that the solid sorbent may also be chosen from the group consisting of natural and synthetic aluminas, clays, charcoals and other known adsorbents. The preferred adsorbents are type 4A, 5A and 13X molecular sieves which will remove oxygen compounds. The terms "sorbent" and "adsorbent" and the terms "sorption" and "adsorption" are commonly and interchangeably used by those skilled in the art.

The regeneration of the adsorbents may include a low temperature hydrogen stripping step in which the temperature of the hydrogen stream is gradually increased. The hydrogen regeneration gas stream preferably contains at least 85 mole percent hydrogen and has an initial temperature below about 200° F. (93° C.). The temperature of the gas stream is gradually increased at a rate less than about 50° F. per hour until a temperature is reached in the range of about 300° to 600° F. (149° to 315° C.). Heated hydrocarbons my then be employed if desired to reach higher regeneration temperatures. This procedure my be utilized to ensure regeneration in the presence of olefins and diolefins on the sorbent. It is also possible that the low temperature hydrogen stripping step may not be required and that conventional regeneration procedures such as pressure reduction and/or initial high temperature hydrocarbon, steam or nitrogen purging may be employed. Regeneration conditions also include a superatmospheric pressure preferably less than about 250 psig. The molecular sieve adsorbents may also be regenerated by calcination in air.

In accordance with the present invention, a resulting stream containing halogenated organic compounds and having a reduced concentration of oxygen compounds is introduced in admixture with a hydrogen-rich, gaseous recycle stream and, optionally, a recycle stream comprising unreacted halogenated organic compounds into a catalytic hydrogenation zone containing hydrogenation catalyst and maintained at hydrogenation conditions. This catalytic hydrogenation zone may contain a fixed, ebullated or fluidized catalyst bed. Moreover, the hydrogenation reaction zone may consist of multiple catalyst beds operated at various conditions. This reaction zone is preferably maintained at conditions which are chosen to dehalogenate the halogenated organic compounds which are introduced thereto. The catalytic hydrogenation zone is preferably maintained under an imposed pressure from about atmospheric to about 2000 psig and more preferably under a pressure from about 100 psig to about 1800 psig. Suitably, such reaction is conducted with a maximum catalyst bed temperature in the range of about 50° F. (10° C.) to about 850° F. (454° C.) selected to perform the desired dehalogenation conversion to reduce or eliminate the concentration of halogenated organic compounds contained in the feed stream. In accordance with the present invention, it is contemplated that the desired hydrogenation conversion includes, for example, dehalogenation and hydrocracking. In addition, the effluent from the hydrogenation zone contains essentially no olefinic compounds or other thermally unstable compounds which may be deleterious to any other further processing steps. Further preferred operating conditions include liquid hourly space velocities in the range from about 0.05 hr$^{-1}$ to about 20 hr$^{-1}$ and hydrogen circulation rates from about 200 standard cubic feet per barrel (SCFB) to about 150,000 SCFB, preferably from about 200 SCFB to about 100,000 SCFB.

As used in the present invention, the term "hydrotreating" or "hydrogenation" is meant to include reactions whereby the organic reactants achieve an increased hydrogen content, regardless of whether this is achieved by olefin saturation, diolefin saturation, desulfurization, denitrification or dehalogenation, for example.

The preferred catalytic composite disposed within the hereinabove-described hydrogenation zone can be characterized as containing a metallic component having hydrogenation activity, which component is combined with a suitable refractory carrier material of either synthetic or natural origin. The precise composition and method of manufacturing the carrier material is not considered essential to the present invention. Preferred carrier materials are alumina, silica, carbon and mixtures thereof. Suitable metallic components having hydrogenation activity are those selected from the group comprising the metals of Groups VIB and VIII of the Periodic Table, as set forth in the *Periodic Table of Elements*, E. H. Sargent and Company, 1964. Thus, the catalytic composite my comprise one or more metallic components from the group of molybdenum, tungsten, chromium, iron, cobalt, nickel, platinum, palladium, iridium, osmium, rhodium, ruthenium, and mixtures thereof. The concentration of the catalytically active metallic component, or components, is primarily dependent upon a particular metal as well as the physical and/or chemical characteristics of the particular hydrocarbon feedstock. For example, the metallic components of Group VIB are generally present in an amount within the range of from about 1 to about 20 weight percent, the iron-group metals in an mount within the range of about 0.2 to about 10 weight percent, whereas the noble metals of Group VIII are preferably present in an amount within the range of from about 0.1 to about 5 weight percent, all of which are calculated as if these components existed within the catalytic composite in the elemental state. It is further contemplated that hydrogenation catalytic composites may comprise one or more of the following components: cesium, francium, lithium, potassium, rubidium, sodium, copper, gold, silver, cadmium, mercury and zinc. Preferred hydrogenation catalysts comprise alumina and palladium.

In accordance with the present invention, the hydrocarbonaceous effluent containing at least one hydrogen halide compound from the hydrogenation zone is cooled and introduced into a vapor-liquid separator to produce a hydrogen-rich, gaseous recycle stream and a liquid stream comprising hydrogenated hydrocarbonaceous compounds and hydrogen halide compounds. In accordance with the present invention, it is contemplated that the vapor-liquid separator is preferably operated at a pressure between about 400 and about 1800 psig and at a temperature from about $-70°$ F. ($-57°$ C.) to about $60°$ F. ($16°$ C.). In one embodiment of the present invention, the resulting liquid stream comprising hydrogenated hydrocarbonaceous compounds and hydrogen halide compounds is separated to produce an anhydrous stream comprising hydrogen halide compounds and a liquid stream comprising hydrogenated hydrocarbonaceous compounds. This second resulting liquid stream is then optionally separated to produce a recycle stream comprising any unreacted halogenated organic compounds which is optionally introduced into the hydrogenation reaction zone and a hydrogenated hydrocarbonaceous stream having a reduced level of halogen. In accordance with one embodiment of the present invention, the hydrogen halide compound is recovered as an anhydrous product stream. This permits the subsequent recovery and use of a desirable and valuable hydrogen halide compound.

In the drawing, the process of the present invention is illustrated by means of a simplified flow diagram in which such details as total number of reaction zone and drier vessels, pumps, instrumentation, heat-exchange and heat-recovery circuits, compressors and similar hardware have been deleted as being non-essential to an understanding of the techniques involved. The use of such miscellaneous appurtenances are well within the purview of one skilled in the art.

DETAILED DESCRIPTION OF THE DRAWING

With reference now to the drawing, a halogenated organic feed stream containing oxygen compounds is introduced into the process via conduit 1 and is contacted with an adsorbent contained in adsorber zone 2 in order to remove at least a portion of the oxygen compound contained in the feed stream. A resulting halogenated organic stream having a reduced concentration of oxygen compounds is removed from adsorber zone 2 via conduit 3 and admixed with an optional hereinafter-described liquid recycle stream provided via conduit 18. The resulting admixture is transported via conduit 4 and is admixed with a hereinafter-described hydrogen-rich gaseous recycle stream provided via conduit 11. This resulting admixture is introduced via conduit 5 into hydrogenation zone 6. The resulting hydrogenated organic stream is removed from the hydrogenation reaction zone 6 via conduit 7, is cooled in heat exchanger 8 and introduced into vapor-liquid separator 10 via conduit 9. A hydrogen-rich gaseous stream is removed from vapor-liquid separator 10 via conduit 11 and recycled as described hereinabove. Since hydrogen is lost in the process by means of a portion of the hydrogen being dissolved in the exiting liquid hydrocarbon and hydrogen being consumed during the hydrogenation reaction, it is necessary to supplement the hydrogen-rich gaseous stream with makeup hydrogen from some suitable external source, for example, a catalytic reforming unit or a hydrogen plant. Makeup hydrogen may be introduced into the system at any convenient and suitable point which is not shown on the drawing. A liquid hydrogenated hydrocarbonaceous stream containing hydrogen and a hydrogen halide in solution is removed from vapor-liquid separator 10 via conduit 12 and is introduced into fractionation zone 13. A product stream containing a hydrogen halide is removed from fractionation zone 13 via conduit 14 and recovered. A liquid distillable hydrogenated hydrocarbonaceous stream is optionally removed from fractionation zone 13 via conduit 15 and introduced into fractionation zone 16. A product stream containing hydrocarbonaceous compounds having a reduced concentration of halogen is removed from fractionation zone 16 via conduit 17 and recovered. A liquid stream containing unconverted organic compounds containing halogen is removed from fractionation zone 16 via conduit 18 and is recycled to hydrogenation reaction zone 6 via conduit 18 as described hereinabove.

EXAMPLE

This example demonstrates the efficacy of processing a halogenated waste stream containing 30 weight percent allyl chloride by-product and 70 weight percent propylene oxide by-product. The characteristics of the halogenated waste stream are presented in Table 1. The halogenated waste stream was contacted with a 4A molecular sieve adsorbent at conditions including atmospheric pressure, a temperature of about 70° F. and a liquid hourly space velocity of about 10. The effluent from the molecular sieve adsorbent was sampled, analyzed and found to have the characteristics presented in Table 1.

TABLE 1

EFFECT OF MOLECULAR SIEVE TREATMENT

| Compound | Mass, % or PPM (Before) | Mass, % or PPM (After) |
|---|---|---|
| Propanal | 491 ppm | <10 ppm |
| $H_2O$ | 184 ppm | <40 ppm |
| Acetonitrile | 84 ppm | <10 ppm |
| Chloropropene | 1650 ppm | 1380 ppm |
| Dichloropropane | 90.8% | 89.7% |
| Benzene | 3000 ppm | 2876 ppm |
| Dichloropropene | 7.58% | 7.29% |

The resulting feedstock which was treated with 4A molecular sieve adsorbent as described above was contacted in a hydrogenation/dechlorination zone with a catalyst containing alumina and palladium at hydrogenation conditions which included a pressure of about 750 psig, a catalyst temperature of about 300° F. and a chloride conversion of 99.9 weight percent. After 1200 hours of operation, the activity, stability and selectivity remained essentially constant. The mechanical equipment associated with the process worked reliably and without a problem during this time period. This operation was continuous with no required downtime for maintenance and no signs of corrosion in spite of the elevated HCl concentrations throughout the process plant The results of the hydrogenation/dechlorination are summarized and presented in Table 2.

TABLE 2

HYDROGENATION/DECHLORINATION SUMMARY
Operating Conditions

| Pressure, psig | 750 |
|---|---|
| Catalyst Temperature, °F. | 300 |
| Chloride Conversion, weight percent | 99.9 |
| Feed Water Content, wppm | 2.5 |
| Weight Hourly Space Velocity, $hr^{-1}$ | 0.3 |

In the event that the feed to the catalytic zone contained higher levels of water and organic oxygen compounds, it could be expected that significant corrosion could occur to both the inorganic oxide catalyst support and the piping downstream of the reactor effluent at points where the feed water and the water resulting from the reaction (organic oxygen compounds are convened to water in the catalytic conversion zone) condense. Corrosion of the catalyst support leads to both loss of catalytic surface area and ultimately the leaching of the catalytic metal, both of which result in loss of conversion performance. Therefore, the conversion performance would not be stable under these conditions. In addition, corrosion piping and equipment downstream of the reactor would have ultimately resulted in equipment failure and operational downtime.

The foregoing description, drawing and example clearly illustrate the advantages encompassed by the process of the present invention and the benefits to be afforded with the use thereof.

What is claimed:

1. A process for treating a halogenated organic stream containing oxygen compounds to produce an anhydrous liquid stream comprising hydrogenated hydrocarbonaceous compounds and a hydrogen halide compound which process comprises the steps of:
    (a) contacting said halogenated organic stream containing oxygen compounds with a selective adsorbent at adsorption-promoting conditions in an adsorption zone to selectively remove at least a portion of said oxygen compounds;
    (b) contacting a resulting halogenated organic stream having a reduced concentration of oxygen compounds produced in step (a) and a hydrogen-rich, gaseous recycle stream with a hydrogenation catalyst in a hydrogenation reaction zone at hydrogenation reaction conditions to increase the hydrogen content of said halogenated organic stream and to thereby produce a hydrogen halide compound; and
    (c) condensing at least a portion of the resulting effluent from said hydrogenation reaction zone to produce said hydrogen-rich, gaseous recycle stream and an anhydrous liquid stream comprising hydrogenated hydrocarbonaceous compounds and a hydrogen halide compound.

2. The process of claim 1 wherein said selective adsorbent is a molecular sieve.

3. The process of claim 2 wherein said molecular sieve is selected from the group consisting of 4A, 5A and 13X molecular sieve.

4. The process of claim 1 wherein said adsorption-promoting conditions include a pressure from about atmospheric to about 500 psig (3448 kPa gauge), a temperature from about ambient to about 160° F. (71° C.) and a liquid hourly space velocity from about 0.1 to about 10 $hr^{-1}$.

5. The process of claim 1 wherein said halogenated organic stream contains compounds having from 1 to about 20 carbon atoms per molecule.

6. The process of claim 1 wherein said halogenated organic stream contains halogenated organic compounds in an mount from about 50 to about 99 wt. %.

7. The process of claim 1 wherein said oxygen compounds are selected from the group consisting of water, aldehydes, ketones, alcohols and ethers.

8. The process of claim 1 wherein said oxygen compounds are present in an amount from about 50 to about 1000 weight ppm.

9. The process of claim 1 wherein said hydrogenation catalyst comprises a Group VIII metal on a refractory inorganic oxide support.

10. The process of claim 1 wherein said hydrogenation catalyst comprises palladium and alumina.

11. The process of claim 1 wherein said hydrogenation reaction zone is operated at hydrogenation reaction conditions including a temperature from about 50° F. (10° C.) to about 8500° F. (454° C.), a pressure from about 100 psig to about 1800 psig and a hydrogen circulation rate from about 200 SCFB to about 150,000 SCFB.

12. The process of claim 1 wherein said halogenated organic stream comprises a component selected from the group consisting of fractionation bottoms from the production of allyl chloride, ethylene dichloride, trichloroethylene, epichlorohydrin and perchloroethylene; by-products from the manufacture of vinyl chloride monomer and propylene oxide, used dielectric fluid containing polychlorinated biphenyls, halogenated benzene, carbon tetrachloride, 1,1,1-trichloroethane, halogenated alcohols, halogenated ethers, chlorofluorocarbons and admixtures thereof.

13. A process for treating a halogenated organic stream containing oxygen compounds to produce a hydrogenated hydrocarbonaceous stream having a reduced level of halogen and an anhydrous stream comprising a hydrogen halide compound which process comprises the steps of:

(a) contacting said halogenated organic stream containing oxygen compounds with a selective adsorbent at adsorption-promoting conditions in an adsorption zone to selectively remove at least a portion of said oxygen compounds;

(b) contacting a resulting halogenated organic stream having a reduced concentration of oxygen compounds produced in step (a) and a hydrogen-rich, gaseous recycle stream with a hydrogenation catalyst in a hydrogenation reaction zone at hydrogenation reaction conditions to increase the hydrogen content of said halogenated organic stream and to thereby produce a hydrogen halide compound;

(c) condensing at least a portion of the resulting effluent from said hydrogenation reaction zone to produce said hydrogen-rich, gaseous recycle stream and a liquid stream comprising hydrogenated hydrocarbonaceous compounds and a hydrogen halide compound; and (d) separating said liquid stream comprising hydrogenated hydrocarbonaceous compounds and a hydrogen halide compound to produce an anhydrous stream comprising a hydrogen halide compound and a stream comprising hydrogenated hydrocarbonaceous compounds.

14. A process for treating a halogenated organic stream containing oxygen compounds to produce a hydrogenated hydrocarbonaceous stream having a reduced level of halogen and an anhydrous stream comprising a hydrogen halide compound which process comprises the steps of:

(a) contacting said halogenated organic stream containing oxygen compounds with a selective adsorbent at adsorption-promoting conditions in an adsorption zone to selectively remove at least a portion of said oxygen compounds;

(b) contacting a resulting halogenated organic stream having a reduced concentration of oxygen compounds produced in step (a), a hydrogen-rich, gaseous recycle stream and a recycle stream comprising unreacted halogenated organic compounds with a hydrogenation catalyst in a hydrogenation reaction zone at hydrogenation reaction conditions to increase the hydrogen content of said halogenated organic stream and to thereby produce a hydrogen halide compound;

(c) condensing at least a portion of the resulting effluent from said hydrogenation reaction zone to produce said hydrogen-rich, gaseous recycle stream and a liquid stream comprising hydrogenated hydrocarbonaceous compounds and a hydrogen halide compound;

(d) separating said liquid stream comprising hydrogenated hydrocarbonaceous compounds and a hydrogen halide compound to produce an anhydrous stream comprising a hydrogen halide compound and a stream comprising hydrogenated hydrocarbonaceous compounds and unreacted halogenated organic compounds; and (e) separating said stream comprising hydrogenated hydrocarbonaceous compounds and unreacted halogenated organic compounds to produce said recycle stream comprising unreacted halogenated organic compounds and said hydrogenated hydrocarbonaceous stream having a reduced level of halogen.

* * * * *